United States Patent [19]

Kikuchi et al.

[11] Patent Number: 4,653,080
[45] Date of Patent: Mar. 24, 1987

[54] X-RAY DIAGNOSTIC APPARATUS

[75] Inventors: Katsuya Kikuchi; Michitaka Honda, both of Tochigi, Japan

[73] Assignee: Tokyo Shibaura Denki Kabushiki Kaisha, Kawasaki, Japan

[21] Appl. No.: 575,549

[22] Filed: Jan. 31, 1984

[30] Foreign Application Priority Data

Feb. 8, 1983 [JP] Japan .................................. 58-20346

[51] Int. Cl.$^4$ ........................ G01N 23/00; G21K 1/12
[52] U.S. Cl. ......................................... 378/7; 378/86; 378/87
[58] Field of Search ....................... 378/7, 86, 87, 159, 378/901, 99; 358/111

[56] References Cited

U.S. PATENT DOCUMENTS

| | | | |
|---|---|---|---|
| 4,081,681 | 3/1978 | Froggatt | 378/7 |
| 4,114,041 | 9/1978 | Oliver | 378/7 |
| 4,149,249 | 4/1979 | Pavkovich | 364/414 |
| 4,217,641 | 8/1980 | Naparstek | 364/414 |
| 4,223,384 | 9/1980 | Hounsfield et al. | 364/414 |
| 4,468,697 | 8/1984 | Verhoeven | 358/111 |
| 4,549,307 | 10/1985 | Macovski | 378/7 |

FOREIGN PATENT DOCUMENTS 0028036 5/1981 European Pat. Off. .
0040158 11/1981 European Pat. Off. .

Primary Examiner—Janice A. Howell
Attorney, Agent, or Firm—Finnegan, Henderson, Farabow, Garrett & Dunner

[57] ABSTRACT

An X-ray diagnostic apparatus comprises, an X-ray radiation source for generating an X-ray and projecting the same toward an object, an X-ray detector for detecting the X-ray which has transmitted through the object to derive a total X-ray intensity signal of the object including a primary X-ray signal component and a scattered X-ray signal component, a signal processor which processes the X-ray intensity signal detected from the X-ray detector in such a manner that a scattered X-ray intensity distribution which is pre-calculated based upon the X-ray intensity signal is eliminated from an X-ray intensity distribution obtained from the X-ray intensity signal so as to derive a distribution function of the primary X-ray signal component without adverse influences on the scattered X-ray signal component, and a monitor for displaying a distribution from based upon the distribution function of the primary X-ray signal component.

6 Claims, 9 Drawing Figures

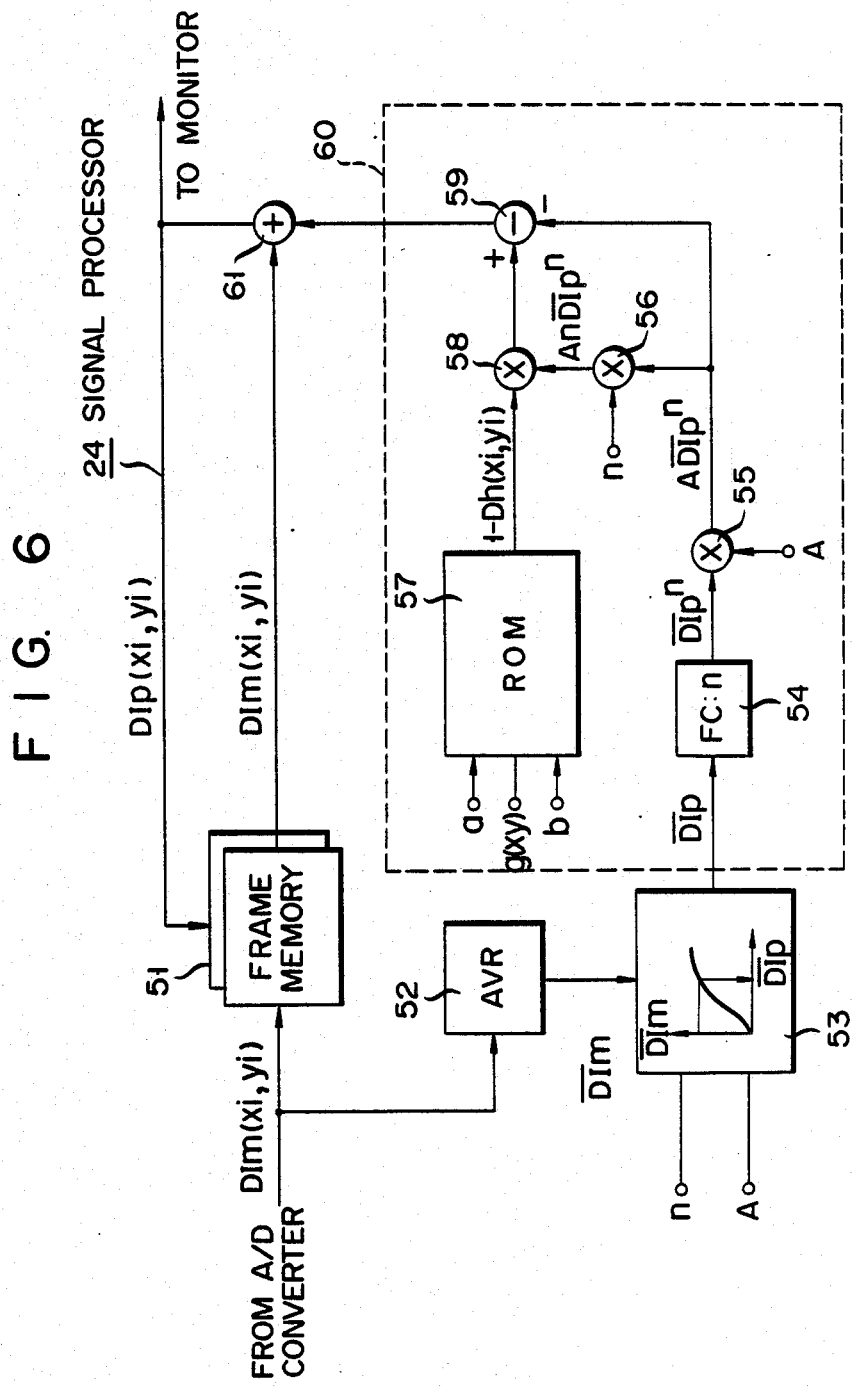

X-RAY DIAGNOSTIC APPARATUS

BACKGROUND OF THE INVENTION

This invention relates to an X-ray diagnostic apparatus in which an X-ray transmission image of an object, e.g., a patient, is available for diagnostic purposes, and more particularly to an X-ray diagnostic apparatus by which an X-ray transmission image of the object is obtained based upon only primary X-rays.

Description of Prior Art:

Generally, in the X-ray diagnostic apparatus set fourth in the preamble, X-rays incident on an X-ray detector contains not only primary X-rays but also scattered X-rays, which are scattered by an object to be examined, e.g., a patient. The scattered X-rays constitute one of the major causes to deteriorate contrast and resolution in the X-ray transmission image. This makes it necessary the elimination of an image component on the scattered X-rays from the X-ray transmission image data as sensed and provided by the detector.

One of the approaches to eliminate the scattered X-ray component is to use a so-called "Buckey Blend" or an elimination grid for scattered X-rays (referred to as a "grid"). This approach also involves a problem that there is a limit in the scattered X-ray elimination, because the grid per se scatters the X-rays incident thereon.

The elimination of the scattered X-rays is of significance in the field of X-ray diagnosis for the reason that it improves image quality, such as contrast and resolution, and thus it allows a logarithm conversion of the primary X-rays image data, thereby obtaining an accurate attenuation quantity of X-rays caused when the X-rays pass through the object. Many studies have been made on the scattered X-rays, aiming at their effective elimination. The complicated phenomena of the scattered X-rays impedes or almost rejects a theoretical approach to this theme. This is the present stage of technology in this field.

For the above background reason, an object of the present invention is to provide by introducing a novel technical idea an X-ray diagnostic apparatus which can effectively eliminate the scattered X-rays image component from the transmission X-ray image components as obtained by the X-ray detector.

SUMMARY OF THE INVENTION

The object of the present invention may be accomplished by providing an X-ray diagnostic apparatus comprising an X-ray radiation source for generating an X-ray and projecting the same toward an object, X-ray detector means for detecting the X-ray which has transmitted through the object to derive an X-ray intensity signal of the object including a primary X-ray signal component and a scattered X-ray signal component, signal processor means which processes the X-ray intensity signal detected from the X-ray detector means in such a manner that a scattered X-ray intensity distribution which is pre-calculated based upon the X-ray intensity signal is eliminated from an X-ray intensity distribution obtained from the X-ray intensity signal so as to derive a distribution function of the primary X-ray signal component without adverse influences on the scattered X-ray signal component, and monitor means for displaying a distribution form based upon the distribution function of the primary X-ray signal component.

BRIEF DESCRIPTION OF THE DRAWINGS

This and other objects and features of the present invention may be best understood by reference to the specification and the accompanying drawings, in which:

FIG. 6 is a schematic diagram of an internal circuit of the signal processor shown in FIG. 5.

DETAILED DESCRIPTION OF THE PREFERRED EMBODIMENT

Before proceeding with the various types of preferred embodiments of the present invention, the principle of the present invention will now be described in detail.

It is assumed that an X-ray incident on an object under examination is generally classified into primary X-rays which directly transmit through the object and enter into an X-ray detector, and X-rays absorbed or scattered by the object through interactions of the X-rays with atoms constituting the object. Those scattered ones are called scattered X-rays. In the energy range of medical X-rays (radiated under 50 KVp–120 KVp of X-ray tube voltage), some causes of occurrence of the scattered X-rays are known, for example, photoelectric effects, Compton effects, Thomson effects, and the like. These phenomena cooperate to cause the scattered X-rays to give adverse effects on the transmission X-ray image to be described later. In general, because the scattered X-rays incident on the X-ray detector experience multi-scattering within the object, it is very difficult to exactly grasp an intensity and a spatial spread of an incident X-ray beam. This phenomenon is explained as follows.

Figure 1:
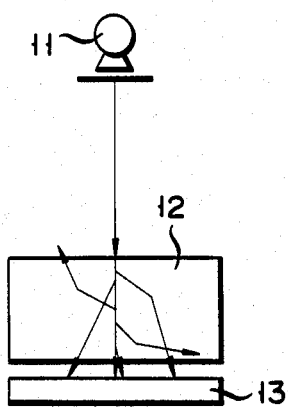
FIG. 1 is an illustration for explaining occurrence of scattered X-rays when an X-ray is projected toward an object under examination.
Figure 2:
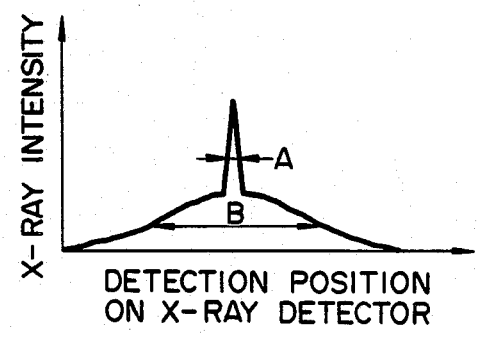
FIG. 2 shows a graphic representation on an X-ray intensity vs. a position on an X-ray detector.

FIG. 1 schematically illustrates how an X-ray radiated from an X-ray source 11 such as an X-ray tube is scattered within an object 12 under examination and reaches an X-ray detector 13 with representing a spatial spread with respect to the detection position of the X-ray detector. FIG. 2 illustrates an X-ray intensity distribution over the detection position of the X-ray detector 13. As seen from FIG. 2, a narrow spread, or spatial distribution of a sharp peak (as indicated by character A) located substantially at the center of the distribution curve is caused by an inherent matter of the diagnosis system, for example, an X-ray focal spot and a wide spread (as indicated by character B) is caused by the scattered X-rays.

In accordance with the study on the scattered X-rays by the inventors, in the present patent application, the following recognition is made that, in the medical X-ray energy range, an intensity distribution of the scattered X-rays emanated from an object with a thickness substantially equal to that of a human body is generally expressed by the following equation;

$$Isc(x, y) = A \int_{-a}^{a} \int_{-b}^{b} f(Ip(x', y'))g(x - x', y - y')dy'dx' \quad (1)$$

Where, Isc(x, y) indicates an intensity distribution of the scattered X-rays over the detection position of the detector. The character A designates a constant. The integration intervals −a to a and −b to b in the above equation define an area projected by the X-rays (referred to as an "X-ray projection area" hereinafter) on the detection position of the detector. More exactly, $-a \leq x \leq a$ and $-b \leq y \leq b$. In the above equation, f(Ip(x, y)) is a function of the primary X-ray intensity distribution Ip(x, y), and g(x, y) is a function defining a spatial spread of the scattered X-rays with respect to the incident X-rays as a pencile beam, and is a so-called "impulse response function".

It is readily understood from the above description that this "impulse response function" means a function for defining the spatial spread of the scattered X-rays with respect to the incident X-rays as the fan-shaped beam or the parallel beam. The function g(x, y) satisfies the following equation (2)

$$\int_{-\infty}^{\infty} \int_{-\infty}^{\infty} g(x, y)dxdy = 1 \quad (2)$$

Generally, A, f(Ip(x, y)) and g(x, y) are determined by a tube voltage and a tube current of an X-ray tube, a thickness of the object, a distance between the object and the detector, and grid conditions respectively.

As seen from the equation (1), an intensity distribution of the scattered X-rays is given by a convolution integration of the function f(Ip(x, y)) relating to the primary X-rays intensity distribution and the function g(x, y) relating to the impulse response. The experiment conducted by the inventors showed that a specific form of the equation (1), as given by the following equation (3), well describes the intensity distribution of the scattered X-rays.

$$Isc(x, y) = A \int_{-a}^{a} \int_{-b}^{b} Ip^n(x', y')g(x - x', y - y')dy'dx' \quad (3)$$

Our study further showed that in the equation (3), A, n and g(x, y) depend on the tube voltage, the tube current, grid conditions, and a distance between the object and the detector, but depend scarcely on the thickness of the object. Of the above factors, n is selected between 0.5 and 1.5. Consequently, the present invention is based on the equation (3) of the scattered X-ray intensity distribution.

The total X-ray intensity distribution Im(x, y) incident on the detector is the sum of the primary X-ray intensity distribution Ip(x, y) and the scattered X-ray intensity distribution Isc(x, y) and is given by $$Im(x, y) = Ip(x, y) + Isc(x, y) \quad (4)$$

If the impulse response function on the X-ray beam's spatial spread due to the system structural factor is given by k(x, y), and the equation (3) is introduced into the equation (4), an equation (5) is obtained:

$$Im(x, y) = \int_{-a}^{a} \int_{-b}^{b} Ip(x', y')k(x - x', y - y')dy'dx' + \quad (5)$$
$$A \int_{-a}^{a} \int_{-b}^{b} Ip^n(x', y')g(x - x', y - y')dy'dx'$$

As described above, the factors, n, A and g(x, y) do not substantially depend on the thickness of the object, but on the tube voltage, the tube current, the grid conditions and the distance between the object and the detector. Therefore, those factors can previously be known by a phantom experiment using a phantom. Alternatively, the factors may be known clinically. Further, the function k(x, y) in the equation (5) can be known, since it is an inherent function belonging to the system. Consequently, the primary X-ray can be calculated by using the factors n, A, g(x, y), and k(x, y), as previously determined in the equation (5), and the total X-ray intensity distribution Im(x, y) actually detected by the detector 3.

An example of the calculations to obtain the primary X-ray intensity distribution Ip(x, y) will be given.

Generally speaking, a variation of the function g(x, y) is very gentle than that of the primary X-ray intensity distribution Ip(x, y) with respect to the detection position. "n" is selected within the range from 0.5 to 1.5. If the first approximation is applied to the Taylor expansion to a mean value $\bar{I}p$ of the primary X-ray intensity distribution Ip(x, y) which is obtained by averaging the intensity distribution Ip(x, y) over the entire x-ray projection area, an equation (6) is obtained $$Ip^n(x, y) \simeq \bar{I}p^n + n\bar{I}p^{n-1}(Ip(x) - \bar{I}p) \quad (6)$$
$$= (1 - n)\bar{I}p^n + n\bar{I}p^{n-1} \cdot Ip(x, y)$$

By using the equation (6), the equation (5) can be rewritten into the following equation (7)

$$Im(x, y) = \int_{-b}^{b} \int_{-a}^{a} Ip(x', y')k(x - x', y - y')dy'dx' + \quad (7)$$
$$A(1 - n)\bar{I}p^n +$$
$$An\bar{I}p^{n-1} \int_{-a}^{a} \int_{-b}^{b} Ip(x', y')g(x - x', y - y')dy'dx'$$

If $\bar{I}m$ is a mean value of the total X-ray intensity distribution Im(x, y) which is obtained to average the intensity distribution Im(x, y) over the entire projection area, the equation (7) gives an equation (8) representing a relation between the mean values $\bar{I}m$ and $\bar{I}p$ $$\bar{I}m \simeq \bar{I}p + A(1 - n)\bar{I}p^n + An\bar{I}p^n \quad (8)$$
$$= \bar{I}p + A\bar{I}p^n$$

Here, it is assumed;

$$\int_{-a}^{a} \int_{-b}^{b} g(x, y)dydx \simeq 1.$$

This relation i.e., the equation (8) can be supported if a spatical spread of the impulse response function g(x, y)

is much smaller than the X-ray projection area. Actually, it is recognized that this relation is satisfied. It may be understand that the mean value $\bar{Im}$ can be calculated from the total X-ray intensity distribution $Im(x, y)$ which can be actually detected. Therefore, by substituting this resultant data $\bar{Im}$ from the equation (8), the desired value $\bar{Ip}$ can be obtained.

Figure 3:
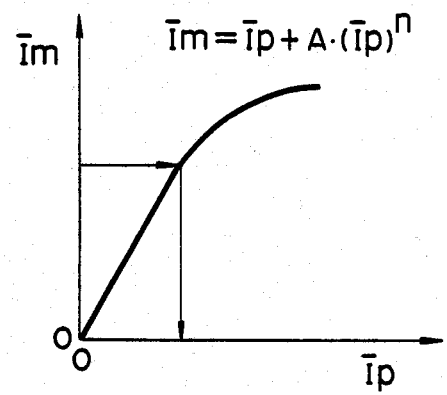
FIG. 3 shows a graphic representation of an $\overline{Im}$-$\overline{Ip}$ relationship.

FIG. 3 is a graphical representation of the equation (8), in which the abscissa represents the mean value $\bar{Ip}$ and the ordinate the mean value $\bar{Im}$ respectively. If the resultant mean value $\bar{Im}$ of the total X-ray intensity distribution is given, the corresponding mean value $\bar{Ip}$ can be obtained from the characteristic curve shown in FIG. 3. Using the $\bar{Ip}$ thus obtained, the equation (7) can further be rewritten $$Im(x, y) = Ip(x, y) + A(1 - n)\bar{Ip}^n + \quad (9)$$

$$A \cdot n \cdot \bar{Ip}^{n-1} \int_{-a}^{a} \int_{-b}^{b} Ip(x', y')g(x - x', y - y')dx'dy'$$

$$\simeq Ip(x, y) + A(1 - n)\bar{Ip}^n + An\bar{Ip}^n h(x, y)$$

$$= Ip(x, y) - An\bar{Ip}^n(1 - h(x, y)) + A\bar{Ip}^n$$

In the above equation, a function $h(x)$ is defined by the following equation:

$$h(x) = \int_{-a}^{a} \int_{-b}^{b} g(x - x', y - y')dx'dy' \quad (10)$$

This function $h(x)$ describes a spatial intensity distribution of the scattered X-rays and can be precalculated from the impulse response function $g(x, y)$. This function may also be depicted as shown in FIG. 4C to be described later. For obtaining the unknown intensity distribution function $Ip(x, y)$, the equation (9) is rearranged to get the following equation (11).

$$Ip(x, y) = Im(x, y) - A\bar{Ip}^n + An\bar{Ip}^n(1 - h(x, y)) \quad (11)$$

An argorithm of an elimination of the scattered X-ray component from the entire incident X-ray components may be summarized as follows.

(1) To calculate the mean value $\bar{Im}$ of the total X-ray intensity distribution $Im(x, y)$ over the entire X-ray projection area.

(2) To substitute the resultant mean value $\bar{Im}$ into equation (8) to obtain the mean value $\bar{Ip}$ of the primary X-ray intensity distribution.

(3) To obtain an intensity distribution $Isc(x, y)$ of the scattered X-ray by using the obtained $\bar{Ip}$ and the A, n and $h(x, y)$, which are predetermined.

Figure 4A:
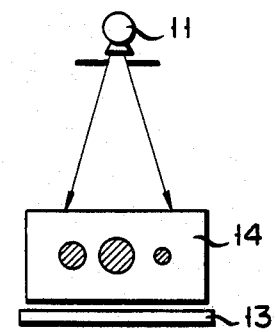
FIGS. 4A–4D are illustrative representations for explaining the principle of the invention.
Figure 4B:
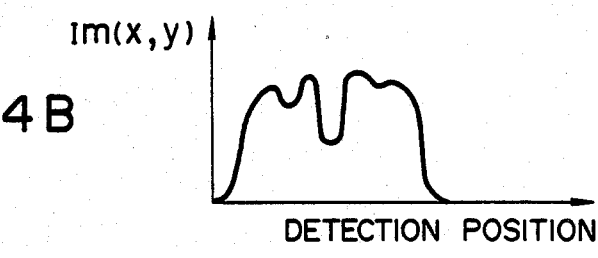
Figure 4C:
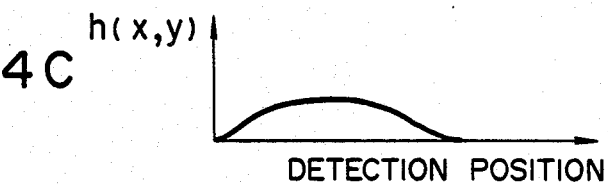
Figure 4D:
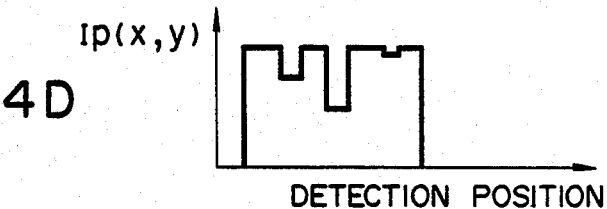
Figure 4D:
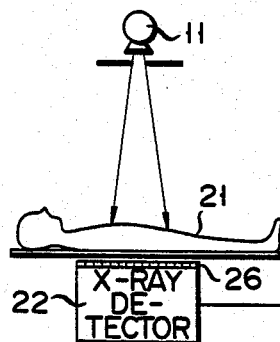

(4) To subtract the scattered X-ray intensity $Isc(x, y)$ from the actually detected intensity $Im(x, y)$ of total X-ray with respect to the detection position $(x, y)$ As the result of the calculation carried out according to the above algorithm, an intensity distribution $Ip(x, y)$ of solely the primary X-ray can be obtained having a distribution as shown in FIG. 4D, for example.

The principle of the present invention will schematically be given referring to FIGS. 4A to 4D.

For detecting X-rays emitted from the X-ray source 11 and then transmitted through a contrast phantom 14 by means of the X-ray detector 13, the total X-ray intensity distribution $Im(x, y)$ of the constrast phantom 14 is observed as an intensity distribution with respect to the detection points of the detector 13 as shown in FIG. 4B. As previously stated, the total X-ray intensity distribution $Im(x, y)$ contains the image information by not only the primary X-ray component but also the scattered X-ray component. For removing the so-called "noise" component due to the scattered X-rays, the scattered X-ray intensity distribution $Isc(x, y)$ as defined by the equation (10) is first obtained, and thereafter the desired intensity distribution $Ip(x, y)$ of the primary X-ray is obtained. This intensity distribution of the primary X-ray intensity distribution $Ip(x, y)$ obtained through the algorithm of removing the scattered X-ray component, is illustrated in FIG. 4D.

One preferred Embodiment of the X-ray diagnostic apparatus according to the present invention will now be described with reference to FIGS. 5 and 6.

Figure 5:
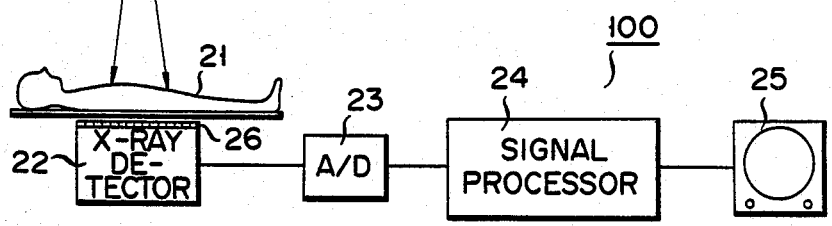
FIG. 5 is a schematic diagram of an X-ray diagnostic apparatus according to one preferred embodiment of the present invention.

FIG. 5 schematically shows a functional block diagram of the X-ray diagnostic apparatus 100 into which the invention with the principle as mentioned above is embodied.

It should be noted that although the apparatus shown in FIG. 5 employs a conventional grid 26, this grid can be omitted so as to realize the present invention in principle.

The X-rays emitted from an X-ray source 11 transmit through a patient 21 as the object to be examined and enter an X-ray detector 22. Then, the detector 22 detects intensities of the incident X-rays as shown in FIG. 4B, to derive a total X-ray intensity signal. An A/D converter 23 converts the detected intensity signal derived from the detector 22 into a digital signal. A signal processor 24 is comprised of a memory for storing image data on the total X-ray intensity signal and an arithmetic means necessary for removing the scattered X-ray component therefrom, as will be described later. Reference numeral 25 designates a monitor for displaying an image of the patient 21 which has no noise caused by the scattered X-ray.

The signal processor 24 will be described in detail referring to FIG. 6. FIG. 6 shows a block diagram of an internal circuit of the signal processor 24. In FIG. 6, the signal processor 24 is comprised of a frame memory 51, a first arithmetic means 52, a second arithmetic means 53, a third arithmetic means 60 and a fourth arithmetic means 61. The frame memory 51 stores every pixel of the digital output signal $DIm(xi, yi)$ derived from the A/D converter 23, which corresponds to the total X-ray intensity distribution $Im(x, y)$. The first arithmetic means 52 averages the signal $DIm(xi, yi)$ over the X-ray projection area to produce a mean value $\overline{DIm}$ thereof. The second arithmetic means 53 previously stores a $\overline{DIm}$-$\overline{DIp}$ curve ($\overline{DIp}$ is a mean value of the primary X-ray intensity distribution $Ip(x, y)$ by averaging it over the entire projection area) as shown in FIG. 3, and produces the corresponding $\overline{DIp}$ on the basis of the output $\overline{DIm}$ derived from the first arithmetic means 52. That is to say, the second arithmetic means 53 carries out the operation of the equation (8). A third arithmetic means 60 calculates an intensity distribution $DIsc(xi, yi)$ of the digital scattered X-rays on the basis of the output $\overline{DIp}$ of the second arithmetic means 53. To be more specific, a function converter 54 raises the output $\overline{DIp}$ of the arithmetic means 54 to the nth power A first multiplier 55 multiplies the output $\overline{DIp}^n$ of the arithmetic means 54 by the constant A. A second multiplier 56 raises the output $A \times \overline{DIp}^n$ of the arithmetic means 55 to the nth power. A ROM 57 stores {1−Dh(xi, yi)} determined by the constants a and b to define the X-ray projection area and the impules response function g(x, y). Here, Dh(xi, yi) represents a digital expression of the equation (10). A third multiplier 58 multiplies the output of the second multiplier 56 and the output of the ROM 57, viz. computes the third term in the equation (11). An arithmetic means 59 receives the output of the first multiplier 55 and the output of the third multiplier 58 to provide A·n·$\overline{DIp}^n$(1−Dh(xi, yi)). In this way, the second and third terms in the equation (11) are computed. A fourth arithmetic means 61 receives the output {A·n$\overline{DI}^n$(1−Dh(xi,yi))} of the third arithmetic means and the X-ray intensity distribution DIm(xi, yi) in a digital form from the frame memory 51, and computes the equation (9) to provide the primary X-ray intensity distribution DIp(xi, yi). The output of the fourth arithmetic means 41 is stored in another frame of the frame memory 51. If necessary, the same output is transferred through a D/A converter (not shown) to the monitor 25 which in turn visualizes an image of the patient 21 based upon only the DIp.

In the X-ray diagnostic apparatus 100 thus arranged, a mean value $\overline{DIm}$ of the total X-ray intensity distribution DIm(x, y) over the entire projection area is computed by the first arithmetic means 52. Using this mean value $\overline{DIm}$, the second arithmetic means 53 computes the mean value $\overline{DIp}$ of the intensity distribution Ip(x, y) of the primary X-ray. The third arithmetic means 60 receives the output of the second arithmetic means to compute the digital scattered X-rays intensity distribution DIsc(xi, yi). Finally, in the fourth arithmetic means 61, the scattered X-rays component is removed from the X-ray intensity distribution DIm, thereby obtaining a primary X-ray intensity distribution DIp(xi, yi) as is effective for an image of the patient 21.

While a specific embodiment of the present invention has been described, the present invention is not limited thereto, but may be modified variously within the scope of the invention.

As seen from the foregoing, by subtracting the scattered X-rays component as previously defined from the X-rays transmitted through the object, an X-ray transmission image formed depends solely on the primary X-rays. Therefore, the following useful effects can be attained:

(1) to improve contrast and resolution of the image of the patient, (2) to exactly obtain an X-ray attenuation quantity by logarithmically converting the image data.

The effect (2) above is more effective particularly for the X-ray diagnosis carried out using an X-ray contrast medium. Specifically, in handling a subtraction image between the images before and after the constrast medium is administered, if the subtraction is performed after both these images are logarithmically converted, it is possible to exactly obtain the product $\Delta\mu\cdot d$ of a change amount $\Delta\mu$ of an X-ray absorption coefficient, which is caused by the contrast medium and the thickness "d" of the tissue under X-ray radiation.

What is claimed is:

1. An X-ray diagnostic apparatus comprising:
  an X-ray radiation source for generating X-rays and projecting the same toward an object;
  X-ray detector means for detecting the X-rays which have been transmitted through the object to derive an X-ray intensity signal of the object including a primary X-ray signal component and a scattered X-ray signal component;
  signal processor means for processing the X-ray intensity signal detected from the X-ray detector means,
  said signal processor means including:
  first memory means for storing a response function of a scattered X-ray intensity response containing a spatial spread of the amount of the scattered X-ray;
  means for calculating a scattered X-ray intensity distribution based upon said function stored in the first memory means and a parameter determined by X-ray radiographic conditions; and
  means for subtracting said calculated scattered X-ray intensity distribution from said X-ray intensity signal of said X-ray detector means so as to derive X-ray intensity signals due to a primary X-ray without adverse influence of the scattered X-ray signal component.

2. An apparatus as claimed in claim 1, further comprising:
  A/D converter means for converting the X-ray intensity signal of the object derived from the X-ray detector means into a corresponding digital X-ray intensity signal to be processed in said calculating and subtracting means.

3. An apparatus as claimed in claim 2, wherein the signal processor means further includes:
  second memory means for temporarily storing the digital X-ray intensity signal derived from the A/D converter means;
  means for averaging the digital X-ray intensity signal with respect to an entire X-ray projection area; and
  second means for calculating an averaged digital value of primary X-ray intensity in response to the averaged digital X-ray intensity signal by way of an approximation on the averaged digital value of the primary X-ray intensity.

4. An apparatus as claimed in claim 3, wherein said second means for calculating includes:
  a function converter in which the averaged digital value of the primary X-ray intensity derived from the second arithmetic means is raised to a predetermined power;
  a first multiplier in which the averaged digital value of the primary X-ray intensity is multiplied by a constant;
  a second multiplier in which the output of the first multiplier is multiplied by the predetermined power;
  a third multiplier in which the output of the second multiplier is multiplied by the predetermined values derived from the first memory means; and
  fifth arithmetic means for calculating the output of the third multiplier and the output of the first multiplier so as to derive the digital scattered X-ray intensity signal.

5. An apparatus as claimed in claim 1, further comprising:
  a grid which is provided in front of the X-ray detector means in such a manner that a part of the X-ray transmitted through the object is absorbed by the same.

6. An apparatus as defined in claim 1, further comprising:
  monitor means for displaying a radiographic image corresponding to said X-ray intensity signal of the primary X-ray data from based upon the response function of the primary X-ray signal component.

* * * * *

UNITED STATES PATENT AND TRADEMARK OFFICE
CERTIFICATE OF CORRECTION

PATENT NO.   :   4,653,080
DATED        :   March 24, 1987
INVENTOR(S)  :   Katsuya Kikuchi et al.

It is certified that error appears in the above-identified patent and that said Letters Patent is hereby corrected as shown below:

Claim 6, line 66, change "from" to -- form --.

Signed and Sealed this

Eighteenth Day of August, 1987

*Attest:*

DONALD J. QUIGG

*Attesting Officer*      *Commissioner of Patents and Trademarks*